(12) United States Patent
Fu

(10) Patent No.: US 12,330,079 B2
(45) Date of Patent: Jun. 17, 2025

(54) SQUIRTING TOY

(71) Applicant: HYCP LLC, Brooklyn, NY (US)

(72) Inventor: Huiying Fu, Brooklyn, NY (US)

(73) Assignee: HYCP LLC, Brooklyn, NY (US)

( * ) Notice: Subject to any disclaimer, the term of this patent is extended or adjusted under 35 U.S.C. 154(b) by 268 days.

(21) Appl. No.: 18/191,243

(22) Filed: Mar. 28, 2023

(65) Prior Publication Data

US 2023/0302375 A1 Sep. 28, 2023

Related U.S. Application Data

(60) Provisional application No. 63/324,242, filed on Mar. 28, 2022.

(51) Int. Cl.

| | | |
|---|---|---|
| A63H 33/00 | (2006.01) | |
| A47G 19/18 | (2006.01) | |
| A61M 11/00 | (2006.01) | |
| A63H 23/10 | (2006.01) | |
| A63H 37/00 | (2006.01) | |
| B05B 11/04 | (2006.01) | |
| B65D 41/06 | (2006.01) | |

(52) U.S. Cl.
CPC .......... *A63H 23/10* (2013.01); *A47G 19/183* (2013.01); *A61M 11/008* (2014.02); *A63H 33/00* (2013.01); *A63H 37/00* (2013.01); *B05B 11/04* (2013.01); *B65D 41/06* (2013.01)

(58) Field of Classification Search
CPC ........ A63H 23/10; A63H 33/00; A63H 37/00; A61M 11/008; A47G 19/183; B05B 11/04; B65D 41/06
See application file for complete search history.

(56) References Cited

U.S. PATENT DOCUMENTS

| | | | | | |
|---|---|---|---|---|---|
| 2,811,283 | A | * | 10/1957 | Bowen | B05B 11/04 222/215 |
| 3,339,770 | A | * | 9/1967 | Weigand | B65D 41/06 215/214 |
| 3,612,324 | A | * | 10/1971 | Malick | B65D 41/06 215/45 |
| 4,739,890 | A | * | 4/1988 | Cooke | B65D 41/06 215/217 |
| 8,622,322 | B2 | * | 1/2014 | Yeager | B05B 11/0029 239/416.4 |
| 9,090,372 | B2 | * | 7/2015 | Warner | B65D 1/0207 |
| 10,273,061 | B1 | * | 4/2019 | Lin | B65D 51/1672 |
| 10,518,948 | B2 | * | 12/2019 | Defert | B65D 35/44 |
| 11,794,961 | B2 | * | 10/2023 | Gamboa Burgos | A61F 9/0008 |

* cited by examiner

*Primary Examiner* — John A Ricci
(74) *Attorney, Agent, or Firm* — Maier & Maier, PLLC

(57) ABSTRACT

A squirting toy including a cap and a body. The body includes a reservoir and a neck, enclosed by an outer wall of varying thickness. Closures are provided on the neck to engage complementary closures on the cap. The cap includes a wall of varying thickness and one or more apertures. The coupling between the body and cap facilitates maintaining the cap coupled to the body under pressure and impact. Segments of the outer walls having increased thickness improve impact resistance and decrease distortion, further facilitating a secure coupling between the body and cap.

20 Claims, 6 Drawing Sheets

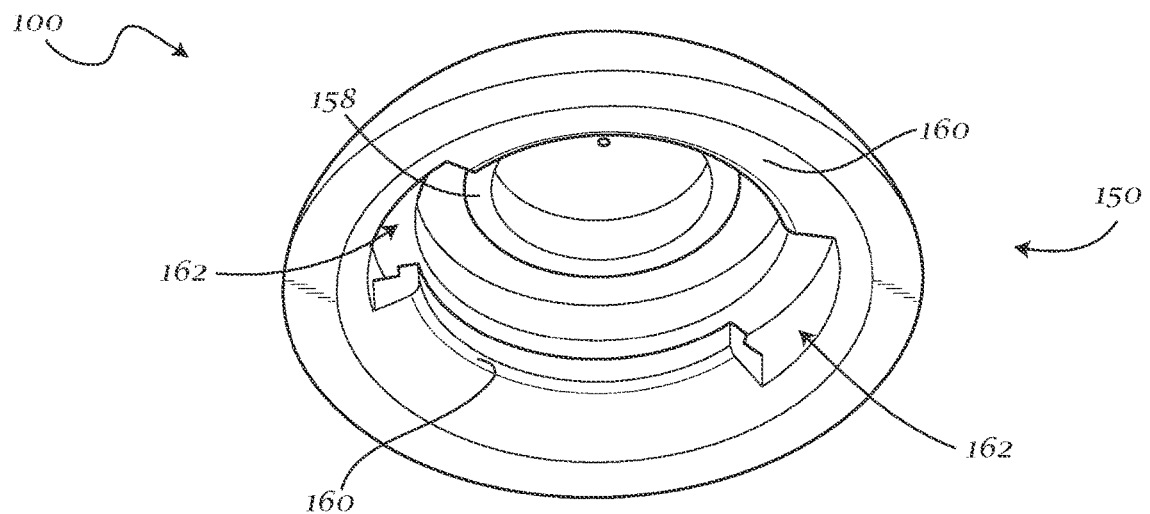
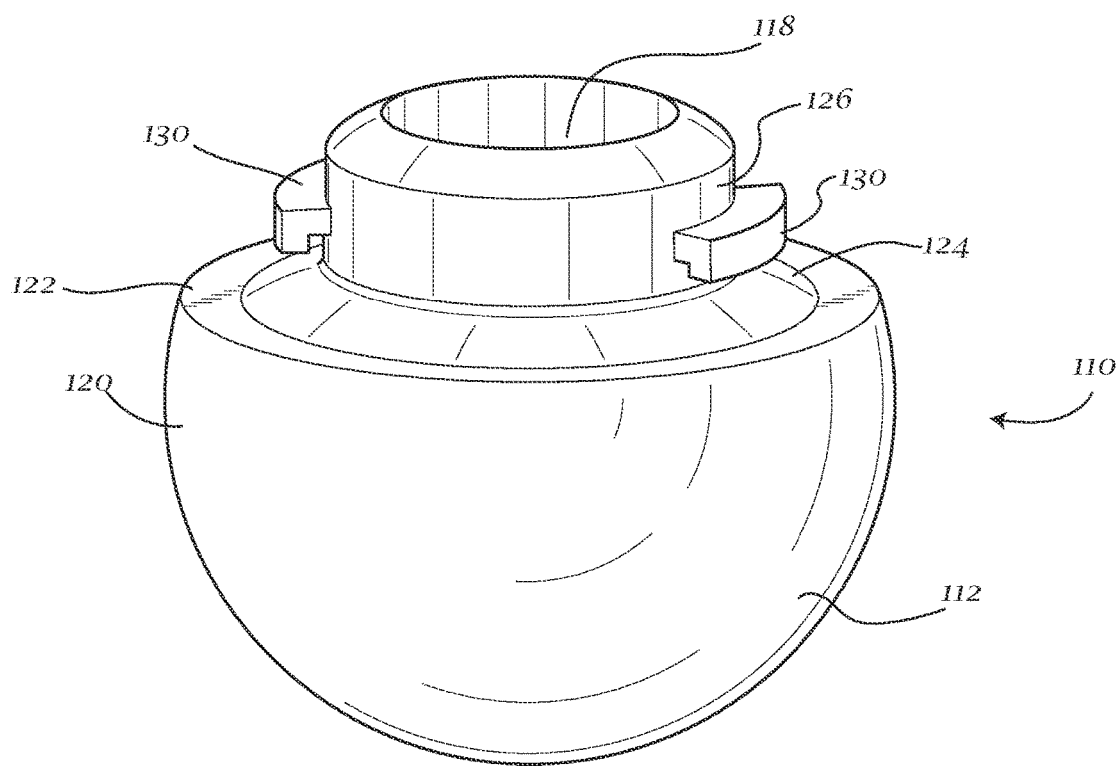
Fig. 1

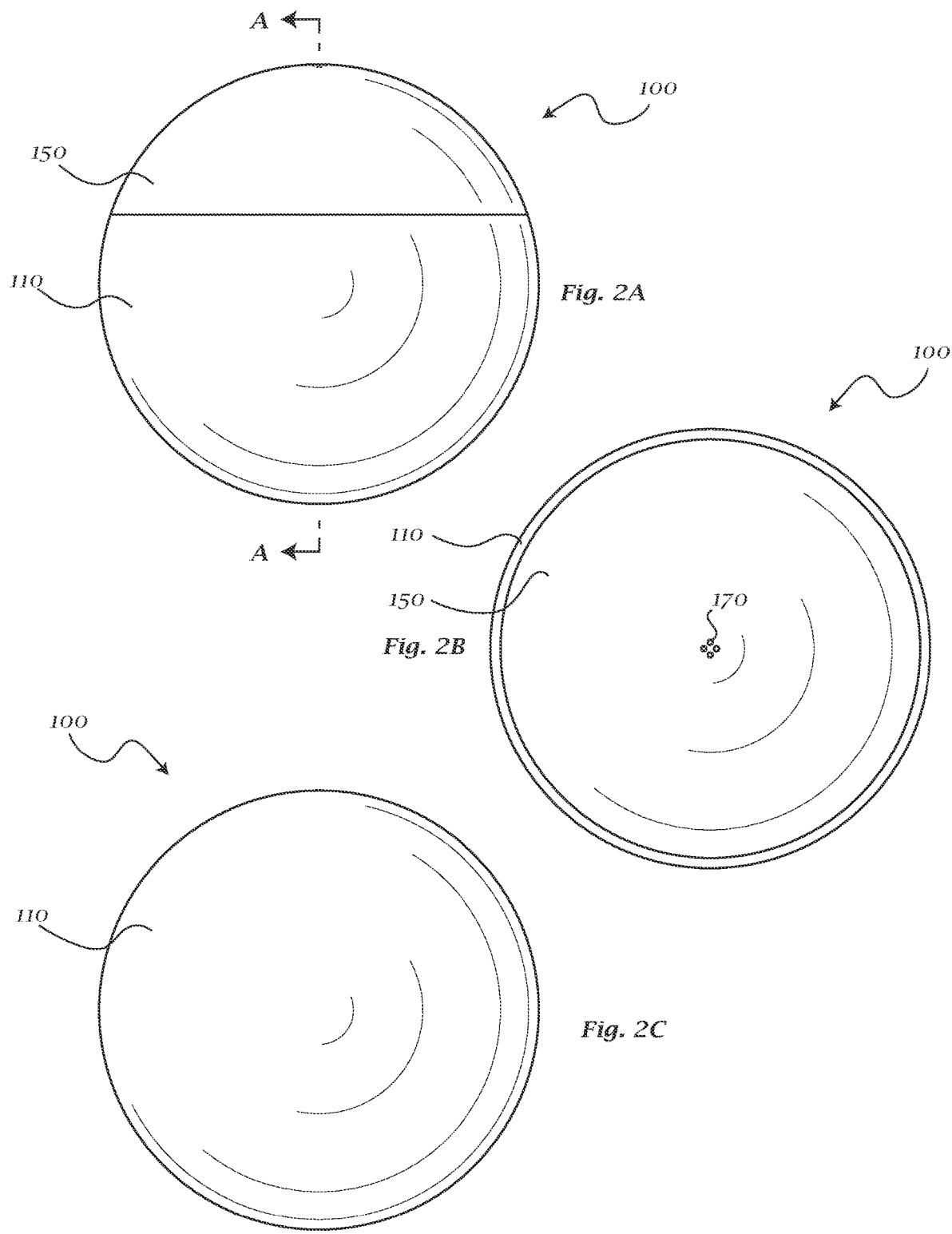

SQUIRTING TOY

CROSS-REFERENCE TO RELATED APPLICATIONS

This application claims priority from U.S. Provisional Patent Application No. 63/324,242, filed on Mar. 28, 2022, entitled "SQUIRTING TOY," the entire contents of which are hereby incorporated by reference.

BACKGROUND

Children's bath toys, such as the ubiquitous "rubber duck," have been around for almost a century. As far back as the 1930s, the rubber duck was conceived as an aquatic toy that could sit either above or below the surface of a bath, which could suck up water into an internal cavity, and which could emit jets of water from the mouth or from other small holes in the rubber duck after doing so. The rubber duck has been followed by numerous other squirting toys following similar design principles, such as handheld "squirting balls" intended to be more portable.

Modern squirting toys fundamentally resemble the original 1930s designs. Squirting toys may be formed most commonly from silicone, either completely (100%) from silicone or with plastic-enhanced closures, though other materials like natural rubber may be used. Since the design has fundamentally changed very little, the problems encountered by these original 1930s designs have also recurred.

For example, parents have often found that squirting bath toys that absorb bath water can quickly begin growing mold. The inner cavity of a squirting bath toy is, in fact, a fairly ideal environment for mold growth; in a bathtub, a squirting bath toy is receiving plenty of water, oxygen, heat, and organic material from the bathwater it absorbs, while the inner cavity of the bath toy is well-shielded from light that could impede mold growth. Since bath toys are intended to be used by children and intended to be child-safe, they cannot be readily treated with chemicals that could impede mold growth, as most mold treatments are toxic. Without a way to safely or effectively clean out the inner cavities of these bath toys, they often must be quickly thrown away.

Some toys exist which can be opened, for example splitting apart into two halves, in order to allow for adequate cleaning. These present a different set of challenges for children to use due to the design issues inherent in having the water toy's cavity be split into multiple parts with obvious seams. For example, such toys often leak water at the closure, or split apart at the closure when squeezed by the child, and often have a much lower low liquid capacity, or conversely, must be much larger and more awkward for the child to use in order to have a similar liquid capacity. The need to frequently refill the toy, the inability to squirt much water out of it, or the greater inconvenience and awkwardness of a larger toy will be unsatisfying to children and lead to a poor squirting experience, frustrating the core goal of a bath toy: getting small children to enjoy bathing. Furthermore, squirting toys that are formed of 100% silicone often use a cap to facilitate squirting, which has further issues. Depending on how tightly this cap must be secured onto the toy, if the design requires the cap be secured loosely then the cap may easily fly off when the ball is squeezed to produce a squirt, and if the design requires the cap be secured tightly then the cap may be too tight for kids to close due to the closure modifications necessary to address the problem of the cap becoming detached from the body. (Potentially, both may be true.)

Water toys and squirting toys include more than just bath toys, and may often be used by children outdoors during the summer. For example, some other commonplace water toys include water balloons and squirt guns. Water balloons are even more disposable than most squirting bath toys, and, because they are intended to explode easily when thrown, often result in significant amounts of small balloon fragments being strewn about an outdoor area, resulting in significant amounts of trash in a manner that is not environmentally friendly. Squirt guns, and other toys with squirting mechanisms, may present issues as well. While squirt guns and similar toys may (in contrast to squeezable bath toys) be formed from hard plastic or from other similar materials, which may be easier to clean if disassembled, squirt guns and the like may be undesirable for other reasons. For example, with squirt guns, many people may be uncomfortable with introducing gun-like objects to their children. Other types of trigger-equipped squirting toys or button-equipped squirting toys may be formed in different shapes in order to avoid this issue, but may themselves suffer from the problem of being difficult for a child to hold or having poor ergonomics.

Accordingly, a squirting toy that solves the above-described issues is desired.

SUMMARY

According to at least one exemplary embodiment, a squirting toy, for example a squirting ball, may be disclosed. In an exemplary embodiment, the squirting toy may have a compressible body and may have a cap having one or more apertures disposed therein. The combination of the compressible body with the cap having apertures may allow water to be squirted from the one or more apertures when the compressible body is squeezed by a user, providing a stream of water in a desired direction. In an exemplary embodiment, the squirting ball toy may be resilient enough to use as a recreational ball, with or without water or other fluid provided therein, while likewise functioning as a water squirting device for summer or bath play.

According to an exemplary embodiment, the configuration of the cap may be such that the connection of the cap to the ball maximizes the amount of ball space available for water storage, while still ensuring that the cap does not become separated from the ball when the ball is being used to squirt water or other liquid, and ensuring that there is a minimal amount of water leakage from the closure. For example, in an exemplary embodiment, it may be contemplated for the cap to be provided with a structure by which the user may secure the cap in place by twisting. It may likewise be contemplated for the cap to be detachable from the body by a large increase in pressure; for example, when the squirting toy is filled with water, it may be contemplated for children to throw the squirting toy against a surface in order to cause the cap to release and in order to cause water to be splashed out of the ball, creating a similar playing experience as a single-use water balloon.

In an exemplary embodiment, the squirting toy may be constructed from silicone, such as food-grade silicone without plastic filler. Such a construction may better ensure safety; for example, it may be contemplated that the toy may be given to a small child or infant that may mouth or teethe on the squirting toy, with the food-grade construction guaranteeing the non-toxicity of the ball. In an exemplary embodiment, since the squirting toy is intended to safely retain liquid and dispense it in a controlled manner, it may be contemplated to have a variant of the squirting toy (for example, a different squirting toy or a version of the squirting toy with an interchangeable cap) that is constructed from food-grade silicone be used for food or drink; for example, it may be contemplated for a cap to have a drinking straw disposed therethrough so that a child may drink out of the squirting toy. (This may, for example, ensure that a child with a habit of throwing or dropping their drinking container causes less damage by doing so.) Such a construction may also ensure that the toy can be cleaned easily by hand or by dishwasher once disassembled, greatly simplifying inspection of the toy and cleaning of the toy and again promoting safety. In an exemplary embodiment, an inner area of the squirting toy may be smooth, again facilitating cleaning and better ensuring that the internal area of the squirting toy dries readily in the dishwasher.

In an exemplary embodiment, a squirting toy may be structured to fulfill other aspects of a child's developmental needs, such as dexterity training, sensory development, gross motor development such as throwing, rolling, catching, and so forth. Accordingly, the squirting toy may be structured to function as an ordinary ball as well as functioning as a squirting toy. In various exemplary embodiments, the cap area of the squirting toy may have more material and so the squirting toy may be slightly unbalanced when used as a ball (for example, if thrown); in other exemplary embodiments, other areas of the squirting toy may be made heavier, for example with the addition of surplus material, via one or more weights, via an insert intended to allow the squirting toy to function more properly as a ball if used as such, or by any other weights or structures that may be added to the squirting toy, such as may be desired. It may likewise be contemplated for the squirting toy to be weighted with the assumption that the squirting toy will be full of water when used as a ball, if desired. In various exemplary embodiments, it may be contemplated for the surface of the squirting toy to be flat and smooth, for the surface to be ridged or mottled to facilitate grip or to encourage sensory development, for the squirting toy to have a variation on a ball shape such as being shaped like a character with one or more arms or legs extending outward from the body of the squirting toy, or as desired.

It may be contemplated for the resilience of the squirting toy to be tuned in order to ensure that the overall body of the squirting toy is soft and bouncy, in order to ensure that the body of the squirting toy is resistant enough to challenge the finger dexterity of small children (such as infants and toddlers) that use the squirting toy as a physical plaything, and in order to ensure that the body of the squirting toy is soft enough that the small child can readily apply force in order to change the ball's shape (for example, in order to squirt water). As noted, food-grade silicone is contemplated as a material, which may for example be non-toxic and odorless, may be naturally mold-resistant, may be biodegradable, and may contain no bisphenol A (BPA), latex, lead, or phthalates. Likewise, it may have high elasticity, may be very resistant to tears, and can withstand very high temperatures, enabling it to be easily cleaned in the dishwasher. Exemplary embodiments of a squirting toy may be modeled to have similar properties to (for example) a baby teether, baby pacifier, or bottle nipple, or any other food-safe silicone product such as a bib or bath product.

Regarding the cap attachment, it may be contemplated that, in a design where the cap is not well-secured to the body of the squirting toy, squeezing of the toy may result in the cap becoming separated from the body of the squeezing toy, resulting in leakage around the seal of the cap or in spillage as the cap becomes decoupled from the body. In particular, it is noted that, when the body of the squirting toy is squeezed in a typical configuration, the neck of the ball body will naturally be pulled inward, which may distort the interface between the ball body and the cap, creating leaks. In certain exemplary embodiments, therefore, it may be contemplated to use a seal configured to have the cap stay on the ball when the ball body is distorted in all possible ways. In various exemplary embodiments, it may be contemplated for the area of the ball body nearest the seal interface with the cap to be thickened in order to reduce possible distortions, it may be contemplated for the cap and the seal interface to be flexible, it may be contemplated for the cap to be provided with a multi-layered seal structure, or any other variation such as may be desired.

It may further be contemplated for the cap to be secured by a seal configured to resist the force of water coming from the ball body, since the squirting toy may function by having the user squeeze the squirting toy in order to increase the pressure inside the squirting toy. In some exemplary embodiments, it may be contemplated for the seal to resist a significant amount of force without popping off; for example, it may be contemplated to configure a cap with a greater number of exit holes (or greater effective area of the exit holes) to use a tighter seal, since there may be an expectation that the user will squeeze the ball with a greater force in order to propel a similar stream of water out of the holes. For example, in a variation in which the cap has only a single hole, the seal between the cap and the body may be less tight than a variation where the cap has three holes, or six; this may, for example, ensure that water is not propelled through the hole at a rate high enough to cause damage, and that the cap will pop off prior to becoming damaged from the pressurized stream distorting the sides of the water outlet hole(s).

It may further be contemplated, in some exemplary embodiments, for the cap to be secured by a seal that may be easy for a small child to replace, though which is not necessarily easy for the small child to remove, if desired. For example, it may be contemplated for a seal to use (for example) a flared or barbed mechanism, such that it can be easily inserted but is more difficult to remove, or such that it might require a particular manipulation of the ball body or of the cap to remove. For example, in an exemplary embodiment, it might be contemplated for the seal elements on the cap to have one or more ribs which are configured to be retained in a groove of the ball body, or for the seal elements to have a groove in which one or more ribs on the ball body are configured to be retained, or some combination of the two. It may likewise be contemplated to have one or more other connection mechanisms, such as a sloping groove facilitating twisting the cap on or off, or another such configuration such as may be desired. In a particular exemplary embodiment, it may be contemplated for a child to be able to close the cap but it may require a stronger individual (e.g. a parent) to open the cap back up, since it may be contemplated that a child may use or even refill the squirting toy without needing to unseal it (e.g. by squeezing an empty squirting toy within the bathtub or another water source) while it may be contemplated that the parent may need to open up the squirting toy in order to clean it or in order to inspect it. In certain exemplary embodiments, it may be contemplated that the toy may be thrown against walls while being used as a ball, in circumstances where the squirting toy is empty and in circumstances where the squirting toy is filled with water, and it may be contemplated for the cap to stay intact when colliding against hard surfaces when thrown with a typical impact force (e.g. with an average toddler throwing force at an average toddler height). It may likewise be contemplated, in some exemplary embodiments, for the cap to pop off when thrown so as to act as a reusable water balloon, and accordingly it may be contemplated to use a weaker seal in such exemplary embodiments.

According to an exemplary embodiment, it may be contemplated for a person to fill the squirting toy by removing the cap (if present and sealed), filling the ball body with water (for example, up to a clear mark indicating a fill line), and then resealing the cap. In some exemplary embodiments, it may be contemplated for a parting line of the squirting toy, between the body and the cap, to be disposed at a height of approximately two thirds of the maximum height of the squirting toy, with the neck of the body extending almost to the top of the height of the squirting toy and the cap providing a protective hemispherical shell that fits over the neck to secure it. This protective hemispherical shell may provide additional protection and cushioning for the body, and may be solid, may be hollow, may have a particular internal pattern, or may have a combination of more than one of these in different areas in the hemispherical shell, such as may be desired.

The user may secure the cap of the squirting toy by, for example, aligning the cap with the ball body, for example aligning particular "keys," or protrusions, on the cap or the body with "keyholes," or slots, of the opposite of the cap or the body. Potentially, "keys" and "keyholes" may be disposed on each of the cap and the body; for example, in one exemplary embodiment, keys may be disposed on one side of the cap and keyholes may be disposed on the opposite side of the cap, and in another exemplary embodiment keys and keyholes may be disposed in a repeating pattern, such as an alternating set of keys and keyholes disposed along the perimeter of the cap and the body.

For example, in one exemplary embodiment, the body may have two "keys," one disposed on either side of the outer perimeter of the body of the neck, which may be protrusions that each extend around a quarter of the outer perimeter of the neck. That is, a first key may be a first protrusion extending from 0 degrees to 90 degrees on the neck, and a second key may be a second protrusion extending from 180 degrees to 270 degrees on the neck, opposite from the first protrusion, while no protrusions are provided in the 90 to 180 degree area or in the 270 to 360 degree area. An opposite configuration may be provided on the cap, with "keyholes" that are configured to accommodate the "keys" of the body being provided over equivalent areas of the cap, from 0 to 90 degrees and from 180 to 270 degrees. Keys and keyholes may be larger or smaller than this, such as may be desired; for example, it might be contemplated instead to have two keys taking up 60 degrees of arc area with equivalently-sized keyholes, two keys taking up 45 degrees of arc area with equivalently-sized keyholes, or any other area configuration such as may be desired. It likewise may be contemplated for the keyholes to be slightly larger than the keys, for example by 5 degrees of arc or more, in order to allow the keys to be more readily inserted into the keyholes and in order to allow the cap to be more readily coupled to the body; for example, in an exemplary embodiment, keys may extend over 45 degrees of the area of the neck or less, and keyholes may extend over 60 degrees of the area of the neck or more, such as may be desired.

Once the user has aligned the keyholes and keys in this manner, the user may then twist the ball body against the cap in either direction in order to have the keys slide into sliding tracks connected to the keyholes, which may fasten the cap to the body and ensure that the key is gripped by both sides of the sliding tracks.

In the above exemplary embodiment, the sliding tracks of the cap, which may be configured to accommodate the keys of the body and retain the keys in position, may be disposed in the 90 to 180 degree area of the cap and the 270 to 360 degree area of the cap. This may allow the cap to be placed over the body with the keys of the body matching up to the keyholes in the cap, allowing the cap to then be twisted in order to dispose the protrusions in the sliding tracks and ensuring that the cap is retained on top of the body.

Other variations on the above exemplary embodiment may also be contemplated. For example, instead of using two keys on the body and two keyholes in the cap, it may be contemplated to use a greater number of keys and keyholes; for example, it might be contemplated to use three keys in a triangle pattern on the neck of the body, four keys centered at the 0, 90, 180, and 270 degree positions on the neck of the body, or any other such configuration. Keys and keyholes may be disposed at regular intervals or may be disposed at irregular intervals, and may be of similar sizes or of different sizes, such as may be desired; for example, in one exemplary embodiment, the body might have two larger keys and two smaller keys disposed around the neck.

Exemplary embodiments of a squirting ball toy disclosed herein can present advantages over known squirting toys. Embodiments disclosed herein may be made of only food-grade silicone without plastic filler; may be safely mouthed by an infant; may be separated and cleaned by hand or dishwasher; may provide interior space for an increased amount of water storage; may provide a secure closure such that the cap portion does not detach when the toy is squeezed for squirting; and may provide a secure closure that minimizes or eliminates water leakage from the interior and through the closure. Further, embodiments disclosed herein may fulfill many aspects of a child's developmental needs, including teething, finger dexterity training, sensory development, and gross motor development such as throwing, rolling, catching, and so forth.

Looking at particular exemplary embodiments of the squirting toy apparatus, it may be contemplated for the squirting toy apparatus to have a body and a cap separable from the body, the combination of which may form a sphere. Each of the body and the cap may be formed homogenously from a synthetic rubber or polymer material. The body may include a lower section which is at least a lower hemisphere of the sphere, with said lower section having a lower section outer wall defining an inner cavity, and an upper section including an upper section outer wall extending from the lower section outer wall that is thicker than the lower section outer wall. The upper section may further have a neck, which may be a hollow cylindrical protrusion extending from the upper section outer wall, which may enclose a neck cavity connecting to the inner cavity of the lower section. The neck may further feature a plurality of closure members disposed at an intermediate height of the neck between a top and bottom edge of the neck and extending radially outward from the neck. The cap may have a cap wall that may be a portion of an upper hemisphere of the sphere, said cap wall having a cylindrical protrusion extending therefrom, said cylindrical protrusion having an outer diameter approximately equal to an inner diameter of the neck and configured to fit within the hollow cylindrical protrusion by extending down into the neck cavity. The cap may further have a groove defined around an outer perimeter of the cylindrical protrusion; and may further define a plurality of cavities extending parallel to the cap wall, each cavity in the plurality of cavities sized to accommodate a closure member in the plurality of closure members.

In an exemplary embodiment, the squirting toy apparatus may be provided as a kit, with the pieces separated from one another, or may be provided as a completed whole. To assemble the kit, according to an exemplary embodiment, a user may align the closure members of the body with the gaps in the cap, insert the cylindrical wall of the cap into the neck of the body, placing it within the neck cavity, and then, once the cap is placed on the body, rotate the cap relative to the body to lock it in place.

In an exemplary embodiment, each of the lower section outer wall, the upper section outer wall, and the neck may be of substantially uniform thickness. The upper section outer wall and the neck may, in some exemplary embodiments, be of the same substantially uniform thickness.

In an exemplary embodiment, the cylindrical protrusion of the cap may be hollow, with a squirting element defined in the center of the cap. (In other exemplary embodiments, it may be contemplated for the apparatus to provide squirting of water by separation of the cap from the body, for example in an embodiment where the apparatus functions as a reusable water balloon, and potentially no squirting aperture may be defined in the cap at all.)

In an exemplary embodiment, each of the plurality of protrusions may be arcuate, with each of the plurality of protrusions having an arc center defined at a center of the neck. For example, there may be two protrusions with each having an identical central angle of between 30 degrees and 90 degrees.

In an exemplary embodiment, each protrusion may be defined opposite another protrusion. For example, in an exemplary embodiment where there are two protrusions, each protrusion may be across from one another.

In an exemplary embodiment, the top of the neck may taper inward, for example to be better aligned with the curve of the cap. In an exemplary embodiment, the cap may define a groove which is equal in thickness or greater in thickness than the neck, and which may be configured to accommodate the neck and has varying depth mirroring a taper of the top of the neck.

In an exemplary embodiment, an outer surface of the sphere formed by the body and the cap may be smooth, though it may be contemplated for either or both to be roughened. For example, in an exemplary embodiment, an area of the cap surface may be roughened to facilitate twisting and closure.

In an exemplary embodiment, the apparatus may be formed from food-grade silicone.

In an exemplary embodiment, an interface between the lower section of the body and the upper section of the body may be a sharp corner, such that an angle, on the external surface of the body, between the lower section of the body and the upper section of the body is at least 90 degrees. In an exemplary embodiment where the lower section comprises at least a lower two-thirds of a sphere, the angle may be greater than 90 degrees.

In an exemplary embodiment, the internal volume of the cap may be solid, though alternatively may be hollow.

In an exemplary embodiment, the cap may further define a second plurality of cavities, each cavity in the second plurality of cavities connected radially to at least one cavity in the plurality of cavities, each cavity in the second plurality of cavities defined in an intermediate zone between an outer surface of the cap and a lower surface of the cap configured to abut the upper section of the body. This set of cavities may define at least one locking groove (for example, a continuous locking groove extending all the way around the cap or individual locking grooves for each cavity), said at least one locking groove having at least one cavity in the second plurality of cavities, said locking groove further having at least one locking protrusion defined around an inner perimeter of the locking groove and extending in a height direction. Each of the plurality of closure members of the upper section of the body may have at least one locking groove defined in the height direction, which may be configured to interlock with the at least one locking protrusion.

BRIEF DESCRIPTION OF THE FIGURES

Advantages of embodiments of the present invention will be apparent from the following detailed description of the exemplary embodiments thereof, which description should be considered in conjunction with the accompanying drawings in which like numerals indicate like elements, in which:

FIG. 1 shows an exemplary embodiment of a squirting toy together with a cap, with the cap separated from the body.

FIG. 2A shows a front view of an exemplary embodiment of a squirting toy as assembled.

FIG. 2B shows a top view of an exemplary embodiment of a squirting toy as assembled.

FIG. 2C shows a bottom view of an exemplary embodiment of a squirting toy as assembled.

DETAILED DESCRIPTION

Figures 3A, 3B:
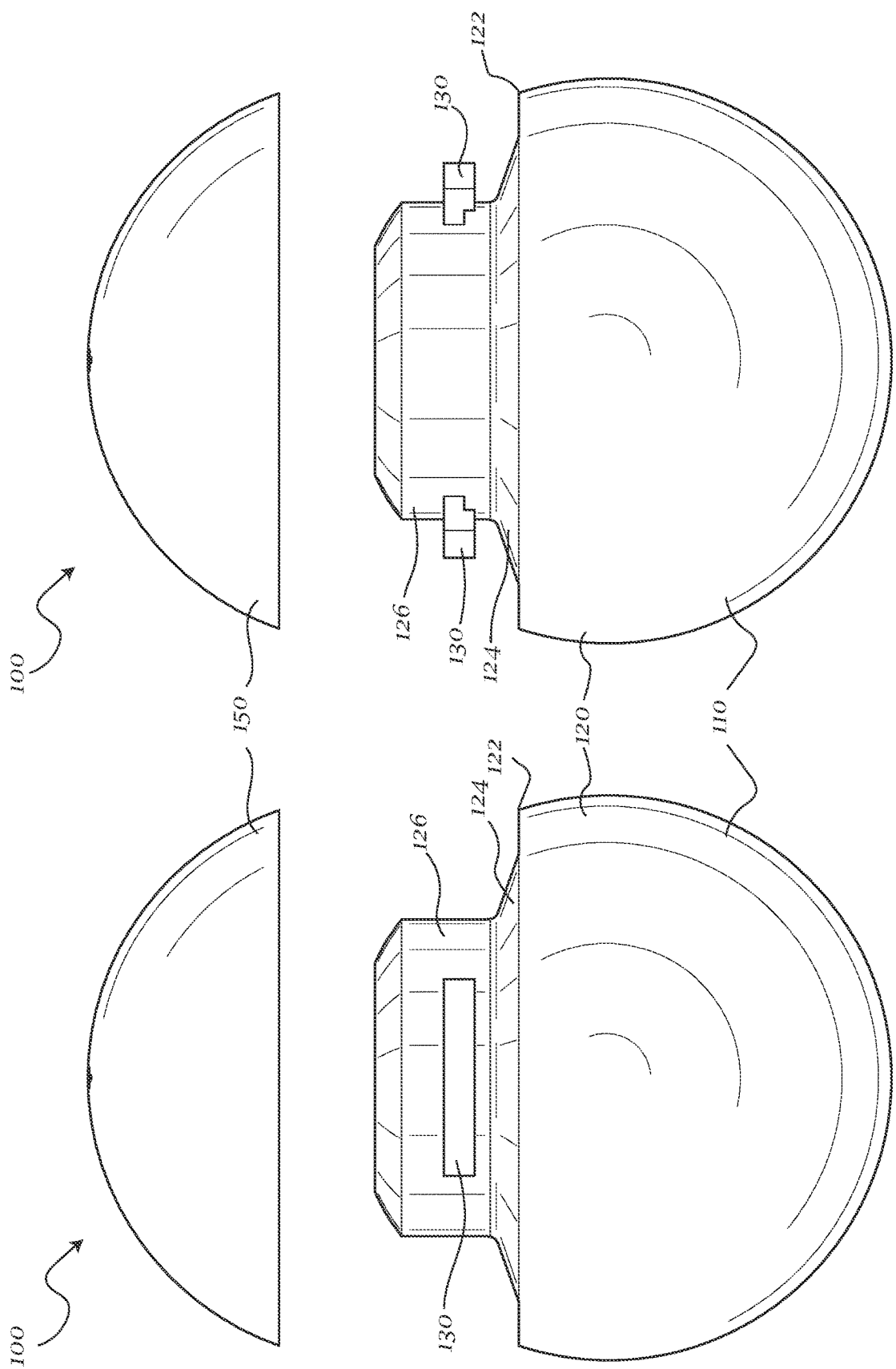
FIG. 3A shows a front view of an exemplary embodiment of a squirting toy with the cap separated from the body.
FIG. 3B shows a side view of an exemplary embodiment of a squirting toy with the cap separated from the body.
Figure 4A:
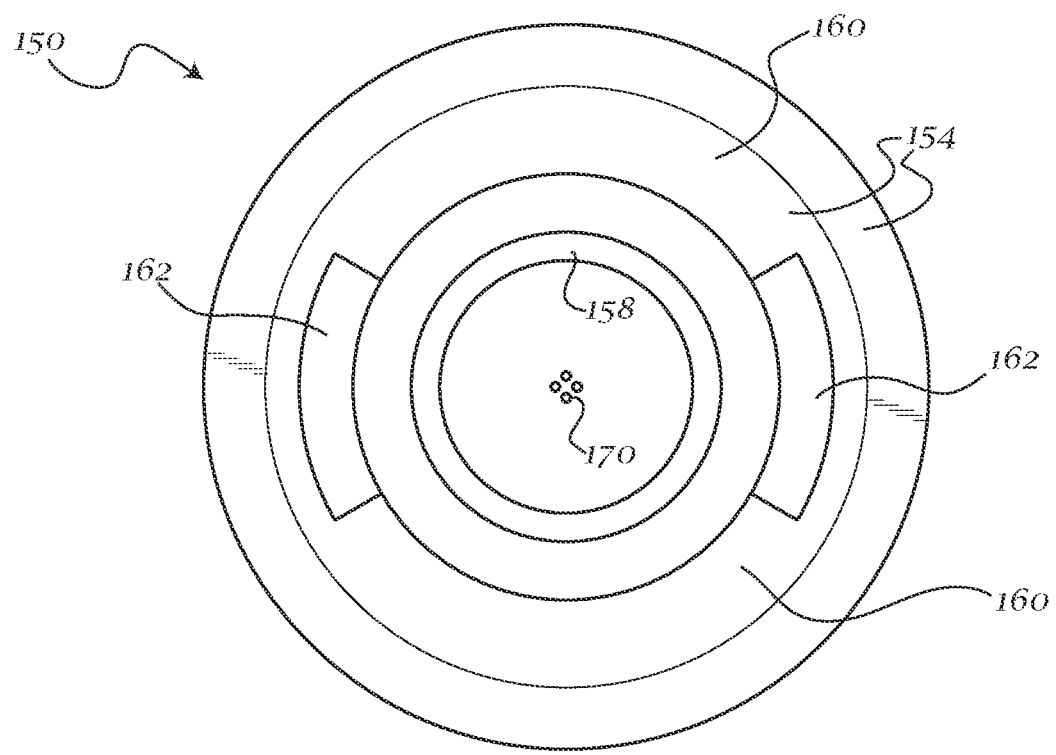
FIG. 4A shows a bottom view of an exemplary embodiment of a cap of a squirting toy.
Figure 4B:
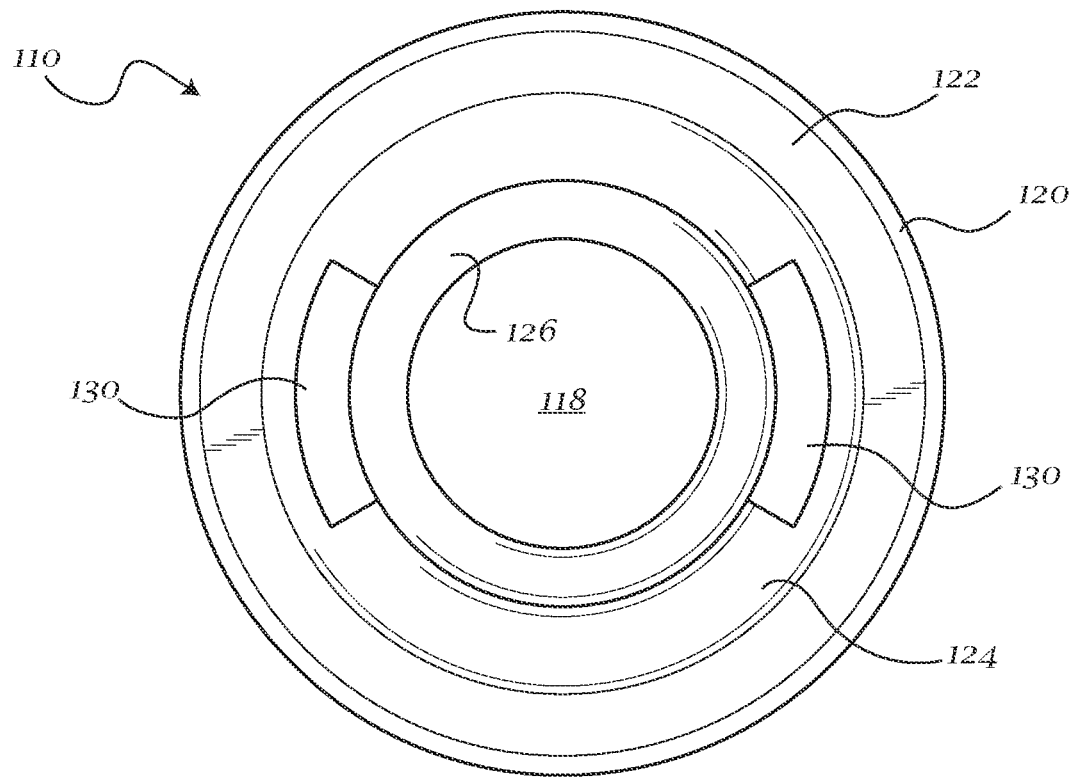
FIG. 4B shows a top view of an exemplary embodiment of a body of a squirting toy.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

According to at least one exemplary embodiment, and as shown in FIGS. 1-5, a squirting ball toy 100 may be disclosed. The toy 100 may include a body 110 and a cap 150. The cap 150 may be coupled to the body 150 by a closure arrangement that enables the squirting ball toy to function as described herein. In an exemplary embodiment, both body 110 and cap 150 may be formed from silicone; however, any other material or combination of materials that enable toy 100 to function as described herein may be contemplated and provided as desired. Silicone rubber, for example, may be relatively elastic (having a relatively low Young's modulus/elastic modulus, usually in the range of around 2 MPa-5 MPa), may be relatively soft, having a Shore Hardness OO value of around ~40 (ranging generally from around 10 to around 80), and may be relatively resilient, having resilience/rebound measurements of around 50%. Various other materials may have comparable properties while also being non-toxic and relatively safe for children to handle; for example, other potential materials might include the flexible materials used in sterile medical gloves, or any of various other rubbers or flexible materials approved by the Food and Drug Administration as food-grade (e.g. synthetic rubbers such as nitrile rubber or EPDM rubber, or synthetic polymers such as polyvinyl chloride).

Looking first at the body 110, according to an exemplary embodiment, it may be contemplated for body 110 to be shaped substantially as a portion of a sphere, though other shapes may be contemplated in other exemplary embodiments. An exemplary embodiment of a body 110 may include an outer wall 112 disposed on an outside of the body 110, an interior chamber 114 in which water or another fluid may be stored, and a neck 118, which may facilitate coupling of a cap 150 to the body.

Figure 5:
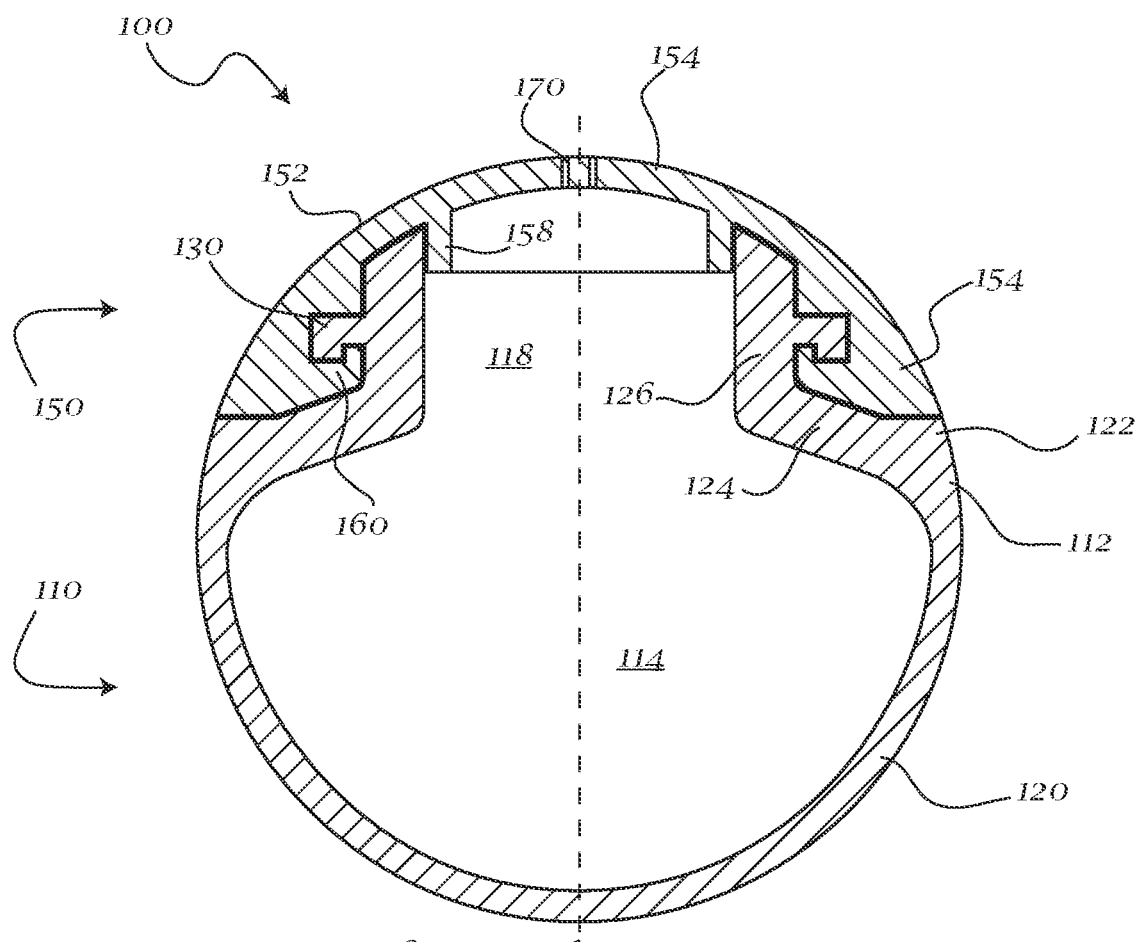
FIG. 5 shows a cross-sectional view of an exemplary embodiment of a squirting toy along line A-A of FIG. 2A.

According to an exemplary embodiment, the outer wall 112 surrounding the interior chamber 114 may have a non-uniform thickness, and may for example be formed of a plurality of segments having varying thicknesses, as shown in the cross-sectional view in FIG. 5. For example, in an exemplary embodiment, outer wall 112 may have a body segment 120 making up the bulk of the outer wall, which may for example take the form of a hemisphere of approximately uniform thickness and form a lower part of the interior chamber. In other exemplary embodiments, it may be contemplated for the body segment 120 to be other than a hemisphere; for example, in an exemplary embodiment where the squirting ball toy 100 is modeled after an American football or other irregularly-shaped ball, it may be contemplated for the body segment 120 to be taller or shorter, to have thicker or thinner portions, or to otherwise vary in size or shape. In another exemplary embodiment, it may be contemplated for the outer wall 112 to have one or more surface features, which may or may not be mirrored in the inner portion of the body segment 120 facing the interior chamber; for example, it may be contemplated for the outer wall 112 to have one or more raised or lowered elements to facilitate grip, such as having one or more raised ridges or having a plurality of dimples like a golf ball, or it may be contemplated for the squirting ball toy 100 to have a shape other than a ball, such as being shaped like a character with one or more arms or legs that may be solid or hollow, and which may extend outward from the outer wall 112. Other variant shapes may be contemplated, such as may be desired.

It may further be contemplated for the outer wall 112 to have a shoulder segment 124, which may, in the exemplary embodiment depicted in FIG. 5, extend inwardly towards a central axis of the sphere 128 that extends through the area of the cap 150; in an exemplary embodiment where the squirting ball toy has another shape, it may be contemplated for a shoulder segment 124 to be disposed toward the central axis of the other shape (e.g. the long axis of a football-shaped embodiment) or to be disposed in another location, as desired. It may further be contemplated for the outer wall to have a corner segment 122 disposed between body segment 120 and shoulder segment 124, and a neck segment 126, which may, in an exemplary embodiment, extend from shoulder segment 124 parallel to the central axis of the sphere. Other variations may likewise be contemplated. For example, in an exemplary embodiment, it may be contemplated for the central axis of the neck segment 126 to be parallel to the central axis of the sphere 128, but may be contemplated for the neck segment 126, in a configuration where the neck segment 126 is formed from flexible material, to have a flared shape, with an outer portion of the neck segment 126 having a wider diameter than an inner portion of the neck segment 126, with the flared end compressing inside the cap 150 to promote a more leakproof connection. It may likewise be contemplated for the neck segment 126 to have one or more elements that are not parallel to the central axis of the sphere 128 at all, if desired; for example, it may be desired to have an angled portion of the neck segment 126 which may be crimped by adding the cap 150.

In an exemplary embodiment, one or more closure members 130 may be disposed at neck segment 126 for engaging a complementary closure member of cap 150. In an exemplary embodiment, the one or more closure members 130 may be, for example, one or more rings extending around the circumference of the neck segment 126, which may be formed from flexible material and which may be configured to fit within a ring-shaped cavity in the cap 150. In an exemplary embodiment where the one or more closure members 130 are one or more rings, it may be contemplated, in various exemplary embodiments, for the rings to be flat or may be contemplated for the rings to have one or more raised elements, such as may be desired, which may help to ensure a better seal.

In an exemplary embodiment, the body segment 120 of the outer wall 112 may have the lowest cross-sectional thickness of all segments of outer wall 112, so as to provide deformability for ease of squeezing the toy at the body segment. In an exemplary embodiment, this may be only a portion of the body segment 120 that has the lowest cross-sectional thickness; for example, in an exemplary embodiment, an equatorial area of the sphere 128 may have a low cross-sectional thickness to facilitate squeezing, while a lower portion of the sphere 128 may be thicker, for example to accommodate a fill site for injection molding, to ensure that the squirting ball toy 100 has additional weight at the bottom in order to ensure that the squirting ball toy 100 lands cap-side-up if thrown, or for another purpose such as may be desired. In an exemplary embodiment, the corner segment 122, which is disposed adjacent to the outer circumference of cap 150 when cap 150 is attached to body 120, may have the largest cross-sectional thickness, and may, for example, have a sharp corner at the outer surface, at the interface of the curved outer surface of body segment 120 and the flat outer surface of corner segment 122. In other exemplary embodiments, it may be contemplated to have a more gradual corner, if desired, for example if appropriate for another shape of the body segment 120. This flat outer surface may be substantially orthogonal to the central axis 128. The sharp angular corner, provided with the increased thickness of outer wall 112, may serve to reduce the effect of shape distortion (for example, from squeezing or from impact) of the ball body to the shape of the neck. Furthermore, the combination of the angular corner and the increased thickness may also provide shock absorption and may create a hard edge so as to impede users from squeezing the toy at the location of corner segment 122 and at cap 150.

In an exemplary embodiment, the shoulder segment 124 and neck segment 126 may have a cross-sectional thickness greater than that of body segment 120 and less than that of corner segment 122. The cross-sectional thickness of shoulder segment 124 and neck segment 126 may be provided so as to sufficiently impede deformation of these segments (for example, from impact or squeezing), and to provide a sufficiently rigid interface and coupling with cap 150. Exemplary cross-sectional measurements can include about 2.5 mm for the body segment, 5 mm for the shoulder and neck segments, and 7 mm for the angle segment. However, these measurements should not be considered as limiting, and any cross-sectional measurements that enable toy 100 to function as described herein can be provided as desired.

Closure members 130 may be provided so at neck segment 126 so as to form a secure closure with cap 150. In an exemplary embodiment, closure members 130 may include a flange extending outwardly from neck segment 128, and a tab extending from the flange, for example substantially orthogonally thereto, so as to define a groove between the tab and neck segment 126. The closure members 130 may thus engage complementary tab-and-groove closure members of cap 150. However, any other closures that enable toy 100 to function as described herein may be contemplated and provided as desired.

Body 110 and cap 150 may be coupled to each other so as to form a sphere. In some exemplary embodiments, the outer surface of cap 150 may form a spherical cap encompassing the upper ⅓ of the outer surface of the sphere, while the outer surface of body 110 may form a spherical cap encompassing the lower ⅔ of the outer surface of the sphere, though other proportions may also be contemplated in other exemplary embodiments. Such dimensions for the body and cap may serve to increase the volume of interior chamber 114 of body 110, thereby increasing the liquid carrying capacity of toy 100. Furthermore, neck 118 may provide yet additional volume, further increasing the liquid carrying capacity of toy 100.

Cap 150 may include an outer wall 152 that may be provided with a plurality of segments, and that may have varying thicknesses corresponding to each of the segments. When body 110 and cap 150 are coupled, a cap segment 154 of outer wall 152 may extend from central axis 128 outwardly until the outer edge of neck segment 126 of outer wall 112. The cross-sectional thickness of cap segment 154 may be substantially similar to the cross-sectional thickness of body segment 120. A sidewall segment 156 may have sufficient thickness such that, when body 110 and cap 150 are coupled, the inner surfaces of sidewall segment 156 are disposed adjacent the outer surfaces of corner segment 122, shoulder segment 124, and neck segment 126 of outer wall 112, except in the areas of the gaps described further below. The outer surface of sidewall segment 156 may be contiguous with the outer surface of cap segment 154 such that the hemispherical cap is formed by the outer surface of outer wall 152 of cap 150.

Sidewall segment 156 may include complementary closure members 160 that are complementary to closure members 130 of body 110, so as to create a secure and water-tight fit between body 110 and cap 150. In an exemplary embodiment, complementary closure members 160 may enclose a groove that may extend around the inner perimeter of the cap, which may be flat and which may allow the closure members 130 of the body to slide within the groove. In an exemplary embodiment, complementary closure members 160 may include a tab-and-groove arrangement that engages the tab-and-groove arrangement of closure members 130 in a complementary manner; for example, a groove may extend around the inner perimeter of the cap 150, and the side of the groove facing the inner perimeter of the cap 150 may have an elevated element functional as a tab in the tab-and-groove arrangement. An exemplary embodiment of such an arrangement may be shown in FIG. 5, which shows tab-and-groove interlocking between the closure members 130 of the body 110 and the complementary closure members 160 of the cap 150.

In an exemplary embodiment, complementary closure members 160 may be separated by gaps 162, which may be sized so as to receive closure members 130 therethrough. For example, each gap 162 may have an arc length of approximately 45°, with closure members 130 having a substantially similar or slightly smaller arc length.

The additional thickness of sidewall segment 156 may serve to provide shock absorption, harden the feel of the cap in the area of the sidewall segment, and impede distortion of the cap in the area of the sidewall segment, thereby providing a secure and water-tight closure. Furthermore, a cylindrical wall 158 may extend into the interior of neck 118, substantially parallel to axis 128, and abutting the interior wall of neck segment 126 of outer wall 112. Cylindrical wall 158 may act as a liquid guard to further reduce the likelihood of liquid penetration between cap 150 and body 110.

Cap 150 may further be provided with apertures 170, which may allow for expulsion of liquid. In one exemplary embodiment, the apertures may be provided substantially at the apex of the cap 150, or may be provided at positions surrounding the apex of the cap 150. In other exemplary embodiments, other dispositions of apertures may be contemplated; for example, it might be contemplated to provide apertures in a line or in a pattern in order to produce a particular spray effect, or it might be contemplated to provide apertures in the area of the cap 150 corresponding to the rim of the neck element 126 in order to better produce a spray effect if the handheld squirting ball 100 is instead thrown. Multiple caps 150 may be provided; for example, in an exemplary embodiment, Any desired number of apertures 170 may be provided, for example, one, two, three, four, or more apertures.

Figure 6:
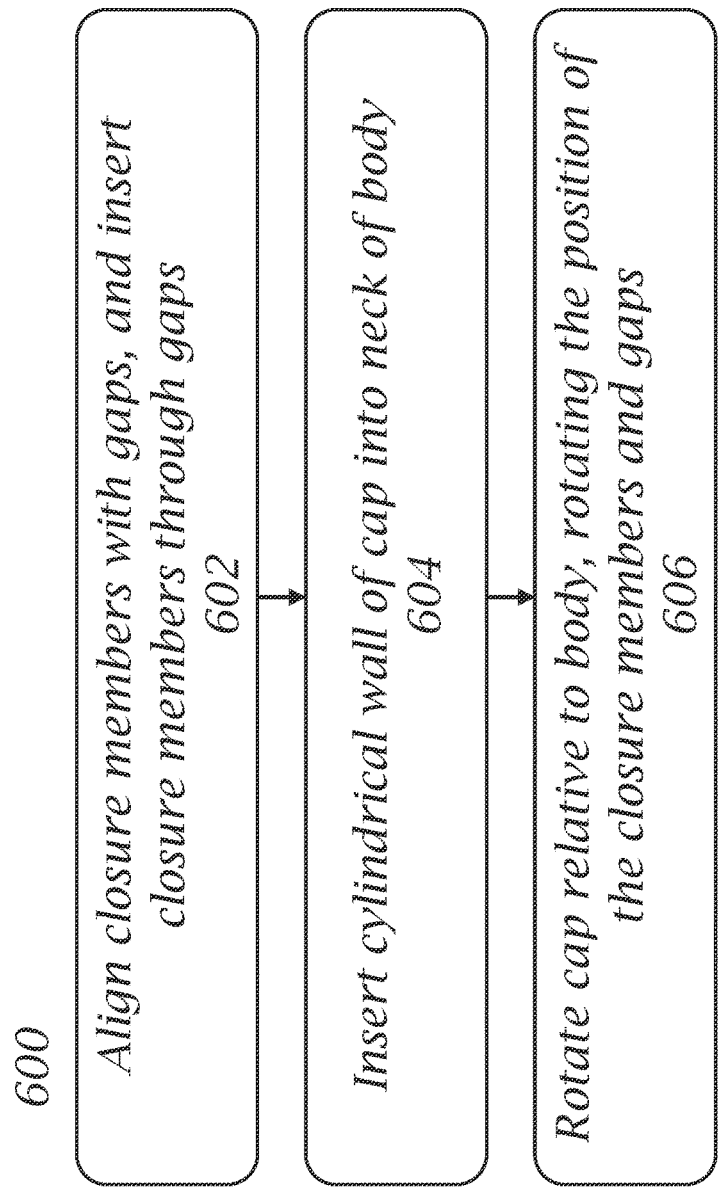
FIG. 6 shows a flowchart depicting an exemplary method of use of an exemplary embodiment of a squirting toy.

FIG. 6 shows an exemplary process 600 for coupling a cap 150 to a body 110. To couple cap 150 to body 110, closure members 130 may be inserted through gaps 162 (step 1, 602), so as to form the spherical shape of toy 100. Simultaneously, cylindrical wall 158 may be inserted into neck 118 (step 2, 604). The combination of these may be suitable to place the cap 150 physically on the body 110, in an unlocked state. Cap 150 may then be rotated relative to body 110 by some amount, for example by 90°, rotating the closure members 130 of the body 110 within the groove arrangement or tab-and-groove arrangement (step 3, 606) such that the closure members 130 of the body 110 become disposed in a position overlapping the complementary closure members 160 of the cap, and the tabs and grooves of closure members 130 and complementary closure members 160 engage each other.

Such a closure configuration can allow body 100 and cap 150 to be securely attached without compromising water capacity or succumbing to strong forces by users, for example when in use by a child, or by impact with the environment. However, any other closures that enable toy 100 to function as described herein may be contemplated and provided as desired.

It should be appreciated that, while the present disclosure discusses a spherical squirt toy, various shapes for the toy may be provided. For example, the toy may have a spherical shape, oval shape, cubic or triangular prism shape, egg shape, and so forth, as well as any decorative shape such as an animal, plant, or object shape, without departing from the spirit of the present disclosure.

Accordingly, the embodiments described herein may provide several advantages. When the cap is coupled to the body, users can use the toy as a ball. It can be rolled, thrown, and played with, without requiring any liquid. For water play, the cap can be detached from the ball body for ease of refills. After the interior chamber is filled with liquid, the cap may be securely fastened by way of the closures on the cap and body. Users can squirt liquid out of the ball during various activities such as bath time or outside in the playground, park, pool, and so forth. Liquid may be squirted for a distance, for example as far as 3-4 feet, depending on the force applied to the ball, creating a similar play experience as a water gun.

The body and cap of the toy may have a soft and bouncy feel. Furthermore, the toy may be resistant enough for infants and toddlers to challenge their finger dexterity but soft enough to allow them to apply force to change the ball's shape.

The toy may be dishwasher safe and heat resistant, and the smooth, curved contour of the inner wall of the interior chamber can reduce the likelihood of water residue when the body placed upside down for drying, thereby enabling an easy cleaning experience. Embodiments formed from silicone can provide easy cleaning and be dishwasher safe.

The design of the closures can provide that the cap remains coupled to the body, even as the neck of the body is pulled inward due to squeezing action applied to the body. Additionally, the closures can provide that the cap remains coupled to the body against the force of the water exiting the interior chamber through the apertures in the cap, and without permitting water to exit at the interface between the cap and the body. Furthermore, the closures can maintain the cap coupled to the body when the ball is thrown and under impact. The closures can also be simple enough for young children to attach and detach the cap themselves.

While one contemplated purpose of an exemplary embodiment provided in the present disclosure is as a spherical squirt toy, alternative exemplary embodiments may be used for other purposes, if desired, for example with some variation in the components. For example, it may be contemplated for one exemplary embodiment of the spherical squirt toy to squirt water out of the cap if thrown against a hard surface to compress the ball body, as well as squirting water if the ball body is manually squeezed to compress the ball body. In such an exemplary embodiment, it may for example be contemplated to have closure members 130 couple less securely to the cap 150, so that the cap 150 can come off more easily if thrown in order to spray out the contents of the ball body at the impact site. (Such an embodiment might entail, for example, a shallower groove for the groove arrangement or tab-and-groove arrangement, or an omission of the tab, or selection of smaller closure members 130, or some other configuration such as may be desired.)

In another exemplary embodiment, since it is contemplated that the spherical squirt toy may be easy to clean and may be safe for an infant or toddler to interact with, for example being formable from food-grade silicone, it may be contemplated for another exemplary embodiment to provide a drinking container for small children, with the present cap 150 design replaced with a version of the cap 150 with a drinking straw extending therethrough. A child may be able to squeeze on the flexible container in order to squirt liquid through the straw into their mouth, while also being able to use the drinking container as a toy.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A squirting toy apparatus, comprising a body and a cap separable from the body, each of the body and the cap formed homogenously from a synthetic rubber or polymer material,
   the body comprising:
   a lower section comprising a lower section outer wall defining an inner cavity; and
   an upper section comprising an upper section outer wall extending from the lower section outer wall that is thicker than the lower section outer wall, the upper section further having a neck comprising a hollow cylindrical protrusion extending from the upper section outer wall, the hollow cylindrical protrusion enclosing a neck cavity connecting to the inner cavity of the lower section, the neck further comprising a plurality of closure members disposed at an intermediate height of the neck between a top and bottom edge of the neck and extending radially outward from the neck;
   the cap comprising:
   a cap wall having a cylindrical protrusion extending therefrom, said cylindrical protrusion having an outer diameter approximately equal to an inner diameter of the neck and configured to fit within the hollow cylindrical protrusion;
   the cap further having a groove defined around an outer perimeter of the cylindrical protrusion; and
   the cap further defining a plurality of cavities extending parallel to the cap wall, each cavity in the plurality of cavities sized to accommodate a closure member in the plurality of closure members.

2. The squirting toy apparatus according to claim 1, wherein the lower section outer wall is of substantially uniform thickness.

3. The squirting toy apparatus according to claim 1, wherein the upper section outer wall and the neck are of substantially uniform thickness.

4. The squirting toy apparatus according to claim 1, wherein the upper section outer wall is of a first substantially uniform thickness, and wherein the neck is of a second substantially uniform thickness different from the first substantially uniform thickness.

5. The squirting toy apparatus according to claim 1, wherein the cylindrical protrusion of the cap is hollow, and wherein at least one squirting aperture is defined within a hollow area of the cylindrical protrusion.

6. The squirting toy apparatus according to claim 1, wherein each of the plurality of protrusions is arcuate, and wherein each of the plurality of protrusions has an arc center defined at a center of the neck.

7. The squirting toy apparatus according to claim 6, wherein the plurality of protrusions comprises two protrusions, each of the two protrusions having an identical central angle of between 30 degrees and 90 degrees.

8. The squirting toy apparatus according to claim 1, wherein each of the plurality of protrusions in the plurality of protrusions is defined opposite another protrusion in the plurality of protrusions.

9. The squirting toy apparatus according to claim 1, wherein a top of the neck tapers inward.

10. The squirting toy apparatus according to claim 9, wherein a groove of the cap is equal in thickness or greater in thickness than the neck, and is configured to accommodate the neck and has varying depth mirroring a taper of the top of the neck.

11. The squirting toy according to claim 1, wherein an outer surface of the body and an outer surface of the cap are smooth.

12. The squirting toy according to claim 1, wherein the synthetic rubber or polymer material is food-grade silicone.

13. The squirting toy according to claim 1, wherein an interface between the lower section of the body and the upper section of the body is a sharp corner, and wherein an angle, on the external surface of the body, between the lower section of the body and the upper section of the body is at least 90 degrees.

14. The squirting toy according to claim 1, wherein a combination of the body and cap is configured to form a sphere, the lower section comprising at least a lower hemisphere of the sphere and the cap wall comprising a portion of an upper hemisphere of the sphere that is less than an entire upper hemisphere of the sphere.

15. The squirting toy apparatus according to claim 1, wherein an internal volume of the cap is solid.

16. The squirting toy apparatus according to claim 1, wherein the cap further defines a second plurality of cavities, each cavity in the second plurality of cavities connected radially to at least one cavity in the plurality of cavities, each cavity in the second plurality of cavities defined in an intermediate zone between an outer surface of the cap and a lower surface of the cap configured to abut the upper section of the body.

17. The squirting toy apparatus according to claim 16, wherein the cap defines at least one locking groove, said at least one locking groove comprising at least one cavity in the second plurality of cavities, said locking groove further comprising at least one locking protrusion defined around an inner perimeter of the locking groove and extending in a height direction.

18. The squirting toy apparatus according to claim 17, wherein each of the plurality of closure members of the upper section of the body has at least one locking groove defined in the height direction and configured to interlock with the at least one locking protrusion.

19. A kit for forming a squirting toy apparatus, the kit comprising a body and a cap separated from the body and configured to be attachable to the body, each of the body and the cap formed homogenously from a synthetic rubber or polymer material, the body comprising:
a lower section comprising a lower section outer wall defining an inner cavity; and
an upper section comprising an upper section outer wall extending from the lower section outer wall that is thicker than the lower section outer wall, the upper section further having a neck comprising a hollow cylindrical protrusion extending from the upper section outer wall, the hollow cylindrical protrusion enclosing a neck cavity connecting to the inner cavity of the lower section, the neck further comprising a plurality of closure members disposed at an intermediate height of the neck between a top and bottom edge of the neck and extending radially outward from the neck;

the cap comprising:
a cap wall having a cylindrical protrusion extending therefrom, said cylindrical protrusion having an outer diameter approximately equal to an inner diameter of the neck and configured to fit within the hollow cylindrical protrusion;
the cap further having a groove defined around an outer perimeter of the cylindrical protrusion; and
the cap further defining a plurality of cavities extending parallel to the cap wall, each cavity in the plurality of cavities sized to accommodate a closure member in the plurality of closure members.

20. A method of assembling a squirting toy apparatus from squirting toy apparatus components comprising a body and a cap separable from the body, wherein each of the body and the cap is formed homogenously from a synthetic rubber or polymer material, wherein the body comprises a lower section comprising a lower section outer wall defining an inner cavity, and an upper section comprising an upper section outer wall extending from the lower section outer wall that is thicker than the lower section outer wall, the upper section further having a neck comprising a hollow cylindrical protrusion extending from the upper section outer wall, the hollow cylindrical protrusion enclosing a neck cavity connecting to the inner cavity of the lower section, the neck further comprising a plurality of closure members disposed at an intermediate height of the neck between a top and bottom edge of the neck and extending radially outward from the neck;

wherein the cap comprises a cap wall having a cylindrical protrusion extending therefrom, said cylindrical protrusion having an outer diameter approximately equal to an inner diameter of the neck and configured to fit within the hollow cylindrical protrusion, with the cap further having a groove defined around an outer perimeter of the cylindrical protrusion, and further defining a plurality of cavities extending parallel to the cap wall, each cavity in the plurality of cavities sized to accommodate a closure member in the plurality of closure members;

wherein the method comprises steps of:

aligning the plurality of closure members of the body with the plurality of cavities of the cap, wherein each closure member in the plurality of closure members is aligned with one cavity in the plurality of cavities;

upon alignment of the plurality of closure members, inserting the cap wall into the neck cavity of the neck; and upon inserting the cap wall into the neck cavity of the neck, locking the cap in place via rotating the cap.

* * * * *